United States Patent
Hakki

(10) Patent No.: US 10,549,092 B1
(45) Date of Patent: *Feb. 4, 2020

(54) SELF-EXPANDING ENDOVASCULAR PACEMAKER SYSTEM

(71) Applicant: A-Hamid Hakki, Dunedin, FL (US)

(72) Inventor: A-Hamid Hakki, Dunedin, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,604

(22) Filed: Jun. 8, 2018

Related U.S. Application Data

(63) Continuation-in-part of application No. 15/691,924, filed on Aug. 31, 2017, now Pat. No. 10,500,394, which is a continuation-in-part of application No. 15/042,301, filed on Feb. 12, 2016, now Pat. No. 9,775,991, which is a continuation-in-part of application No. 13/649,792, filed on Oct. 11, 2012, now Pat. No. 9,289,593.

(60) Provisional application No. 61/545,913, filed on Oct. 11, 2011.

(51) Int. Cl.
  *A61N 1/05* (2006.01)
  *A61N 7/00* (2006.01)
  *A61N 1/362* (2006.01)
  *A61N 2/00* (2006.01)

(52) U.S. Cl.
  CPC ............ *A61N 1/057* (2013.01); *A61N 1/362* (2013.01); *A61N 7/00* (2013.01); *A61N 2/004* (2013.01); *A61N 2007/0004* (2013.01); *A61N 2007/0026* (2013.01)

(58) Field of Classification Search
  CPC .................................................. A61N 1/3756
  See application file for complete search history.

(56) References Cited

U.S. PATENT DOCUMENTS

| | | | | |
|---|---|---|---|---|
| 5,282,845 A | * | 2/1994 | Bush | A61N 1/0587 607/127 |
| 2003/0092977 A1 | * | 5/2003 | Sahatjian | A61B 5/02007 600/381 |
| 2004/0176672 A1 | * | 9/2004 | Silver | A61B 5/0031 600/345 |

* cited by examiner

*Primary Examiner* — Alyssa M Alter
(74) *Attorney, Agent, or Firm* — Rosenberg, Klein & Lee

(57) ABSTRACT

A system applies and senses electrical energy to and from tissue within a patient's body. The system includes a steerable delivery catheter, housing a flexible shaft and an electrical generator disposed on or embedded within the flexible shaft. Electrodes coupled to the shaft self-expand radially from a compressed position to an expanded position once the delivery catheter is withdrawn, thereby contacting a wall of the tissue of the patient's body to conduct electrical or other signals. The system may be inserted into the coronary sinus and tributary vein to provide physiological pacing to the His bundle and left ventricle. Further, the system provides for controlled passive transmission of normal electric impulses from the atria to the His bundle and ventricles without the need for an embedded generator.

20 Claims, 3 Drawing Sheets

SELF-EXPANDING ENDOVASCULAR PACEMAKER SYSTEM

REFERENCE TO RELATED APPLICATIONS

This application is a continuation-in-part of co-pending U.S. patent application Ser. No. 15/691,924, filed on 31 Aug. 2017, which was a continuation-in-part of U.S. patent application Ser. No. 15/042,301, filed on 12 Feb. 2016 and now issued as U.S. Pat. No. 9,775,991, which was a continuation-in-part of U.S. patent application Ser. No. 13/649,792, filed on 11 Oct. 2012 and now issued as U.S. Pat. No. 9,289,593, which was based on Provisional Patent Application No. 61/545,913, filed on 11 Oct. 2011. All of the above applications are incorporated herein by reference.

FIELD OF THE INVENTION

The invention relates to the field of cardiology and in particular to systems for pacemakers and defibrillators. More in particular, this invention is directed to the field of treatment of abnormal heart rhythm through cardiac pacing or shocking. Still further, the present system relates to the field of leadless systems for providing pacing of the tissue by an intravascular self-expanding electrode system, and an embedded generator able to detect electrical and nonelectrical cardiac and extra-cardiac input for inducing electrical and mechanical cardiac action.

BACKGROUND OF THE INVENTION

Conventional cardiac pacemakers and defibrillators generally consist of a round disc shaped generator for electrical stimulation and an elongated flexible wire lead that is connected proximally to a header structure on the generator that is implanted subcutaneously for cardiac pacing and defibrillation. The cardiac lead is generally configured with tubular electrically insulated sleeve structures that are inserted into the body through an incision overlying veins leading to the heart chambers where the distal end of the lead is lodged. In such cases, the distal end of the lead is connected to a tubular tip electrode, having an increased diameter forming an annular shoulder against which the distal end of the sleeve abuts.

Biocompatible silicone based adhesives are generally used to connect the distal end of the lead sleeve and the tip electrode. Among the limitations of adhesives is that the manufacture of the assembled lead requires sufficient time for the adhesive to cure, and the adhesive's bond strength may decrease in time and permit separation from the tip electrode from the sleeve. Fixing the distal end of the lead to cardiac tissue is accomplished generally by conventional anchoring systems. One such active fixation mechanism involves a screw-in electrode. Further, a passive fixation mechanism is sometimes used, consisting of one or more radial tines that engage the inner lining of the heart or blood vessel.

Such conventional devices are typically employed and include a single chamber device as well as a dual chamber device. The single chamber device is capable of sensing and pacing in one chamber, either in the atrium or in the ventricle. Dual chamber devices have the capability of sensing and pacing in both chambers. Modes of pacing are designated, for example, VDD, DVI, VVI, and DDD, where the first letter of the mode indicates the chamber being paced, the second letter indicates the chamber being sensed, and the third letter indicates inhibited or triggered responses. A fourth letter "R" may denote rate responsive pacing to match a patient's activities. In addition to pacing the right/atrium and ventricle pacing, the left ventricle by way of the cardiac veins or biventricular pacing provides a physiologic and synchronous cardiac contraction which would improve cardiac function.

Generally speaking, there are two types of leads in the art: unipolar and bipolar leads. The unipolar lead has a single conductor coil, typically with a cathode, or negative pole, at the distal tip and an anode, or positive pole, defined by the housing of the stimulator. Electric current returns to the anode via body tissue as a current path. In opposition, a bipolar lead has two conductor coils, the distal tip forming the cathode and an annular or ring electrode located a few millimeters proximal to the distal tip. High voltage defibrillation is delivered by the one or two shocking coils that are inserted intravenously.

Pacemaker leads that have been used are generally suited for placement in the ventricle and atrium. In order to provide permanent pacing and to avoid pacemaker lead dislodgement, various methods have been used for anchoring the leads to the endocardium, the inner lining of the heart chambers.

Prior art leadless pacemakers include limitations wherein the devices require an anchoring system in the form of screws or tines. In particular, the Nanostim device (St. Jude Medical) uses a helical wire screw; while the Micra system (Medtronic) uses tines, and is delivered to the right ventricle by way of the femoral vein, having a reattachable mechanism for extraction. Such devices solely pace the ventricle and thus do not permit atrioventricular synchrony. In particular, the Micra transcatheter pacemaker is a single-chamber ventricular pacemaker that is self-contained in a hermetically enclosed capsule. The implantation procedure for the transcatheter pacemaker uses a steerable catheter delivery system and is inserted through a femoral vein by use of a 23-French introducer. Such leadless prior art devices do not supplant traditional lead-containing transvenous pacemakers, and are generally used only for single-chamber ventricular pacing. This procedure is generally reserved for patients with atrial fibrillation and bradycardia or for use in patients who only need infrequent pacing. Such prior art systems are not useful in the treatment of the majority of pacemaker recipients that include patients with sinus-node dysfunction or heart block and do not have a role in the treatment of patients with heart failure who need left-ventricular resynchronization for improvement of cardiac output. (M. S. Link, "Achilles' Lead: Will Pacemakers Break Free?" N. Engl. J. Med., Vol. 374, No. 6 (Feb. 11, 2016), pp. 585-586).

Other leadless pacemaker devices are shown in U.S. Pat. Nos. 5,814,089, 6,522,915, 6,584,352, 8,923,963, and 9,072,914. However, such prior art systems are generally not self-retaining and require fixation tines or helical fixation when inserted into a patient's body. Such prior art systems generally do not provide for an adjustable diameter size and have limited endothelial contact.

PCT Publication WO2004/045675 discloses an introducer through which a pacemaker lead is guided. This introducer is formed with a distal end comprising an anchor attached to the walls of the cardiac chambers. Through use of such prior art introducers, there is permitted steering of the pacemaker lead, and the pacemaker is prevented from displacements or folding onto itself due to the lack of support.

Another prior art system, U.S. Pat. No. 6,654,683, discloses an ultrasonically activated implantable cardiac electrode system, whereby piezoelectric elements convert mechanical energy into electrical energy sufficient to cause pacing of the cardiac tissue. Mechanical energy may originate from an external source low frequency ultrasound transmitter. The electrical energy produced by the piezoelectric element delivers pacing level electrical energy between the system's anode/cathode. Active fixation elements using tines, hooks, and barbs are provided. The prior art system does not use the data to send signals to a wireless curvilinear electrode configuration and thus, the curvilinear electrodes do not require a power source, since the generator functions as the sensing system and provides the logic necessary to synchronize the stimulation of tissues. An algorithm is used for determining the timing and sequence of stimulation of cardiac tissues for generators attached to the electrode wires embedded in the cardiac chambers.

Finally, U.S. Pat. No. 6,256,543 discloses a temporary pacemaker lead having a pair of connections with releasable engagement so as to permanently affix the electrode to the heart tissue. The electrode may be in the form of a piece of metal, such as a clip, and when the lead wire is removed from the heart, such is released from the electrode and may be reattached.

SUMMARY OF THE INVENTION

It is an object of the disclosed system to firmly anchor electrodes of a pacemaker system against a tissue wall, while still permitting easy de-anchoring and removal of the pacemaker system.

It is another object of the disclosed system to control the conduction of pacemaker signals through a heart vessel, so as to activate an atria sufficiently in advance of activation of a ventricle in order that the ventricle is filled before ventricular contraction begin.

It is still another object of the disclosed system to pace tissue of multiple heart chambers without traversing heart valves.

It is yet another object of the disclosed system to operate without an internal battery which requires regular replacement.

These and other objects may be attained in a self-expanding endovascular pacemaker system. In accordance with certain embodiments of the present invention, a system is provided for applying and sensing electrical energy to and from tissue within a patient's body. The system includes a flexible shaft insertable within the patient's body, a plurality of self-expanding electrodes each physically coupled to the shaft and electrically coupled to an electrical source, and a steerable delivery catheter for insertion into a vascular system. The shaft defines a shaft axis line. Each electrode is radially expandable with respect to the shaft axis line from a compressed position to an expanded position, and is configured to conduct electrical signals from the electrical source into a wall of the tissue of the patient's body when in contact with the wall. The delivery catheter surrounds the electrodes and the shaft and applies pressure to the electrodes to thereby restrain the electrodes in the compressed position while within the delivery catheter. The electrodes and the shaft are removable from the delivery catheter, and the electrodes elastically self-expand to the expanded position when removed from the delivery catheter.

In accordance with other embodiments of the present invention, a system is provided for applying and sensing electrical energy to and from tissue within a patient's body. The system includes a flexible shaft insertable within the patient's body, an electrical source embedded within the shaft, and a plurality of self-expanding electrodes each physically coupled to the shaft and electrically coupled to the electrical source. The shaft defines a shaft axis line. Each electrode is radially expandable with respect to the shaft axis line from a compressed position to an expanded position, and is configured to conduct electrical signals from the electrical source into a wall of the tissue of the patient's body when in contact with the wall.

In accordance with still other embodiments of the present invention, a system is provided for applying and sensing ultrasound energy to and from tissue within a patient's body. The system includes a flexible shaft insertable within the patient's body, an ultrasound energy source embedded within the shaft, and a plurality of self-expanding electrodes each physically coupled to the shaft and electrically coupled to the ultrasound energy source. The shaft defines a shaft axis line. Each electrode is radially expandable with respect to the shaft axis line from a compressed position to an expanded position, and is configured to conduct ultrasound energy signals from the ultrasound energy source into a wall of the tissue of the patient's body when in contact with the wall.

Additional aspects, details, and advantages of the disclosed system and method will be set forth, in part, in the description and figures which follow.

DETAILED DESCRIPTION OF THE PREFERRED EMBODIMENTS

Figure 1:
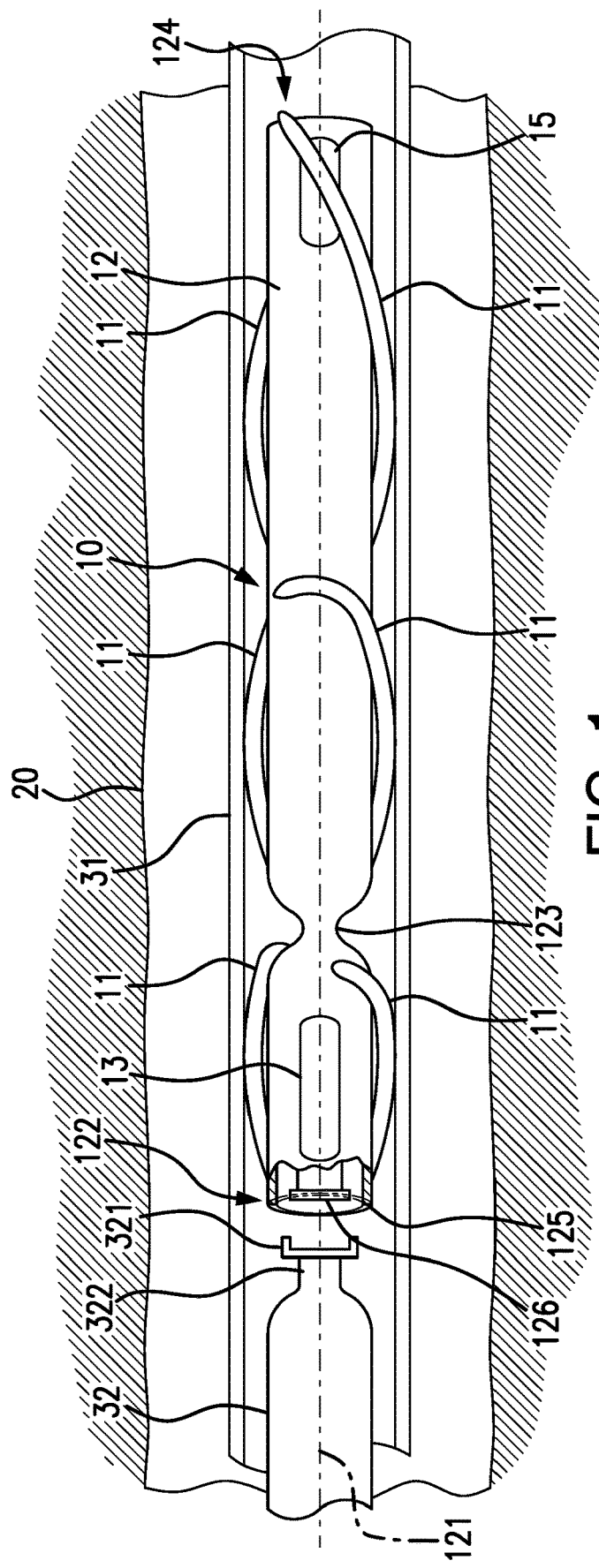
FIG. 1 is a schematic perspective view illustrating a system for generating and sensing electrical energy to and from tissue within a mammalian body, in a pre-deployment configuration, according to an embodiment of the invention.

The following description with reference made to the accompanying figures is not to be interpreted in a limited sense. It is to be noted that other embodiments may be utilized without departing from the scope of the current invention, as defined in the Claims appended to this description.

The following disadvantages of the prior art, among others, are noted:

1. Treatment of symptomatic bradycardia is generally provided through cardiac pacing using surgically inserted subcutaneous generators in conjunction with one or more transvenous leads that provide electrical pacing to the cardiac conduction system. However, complications arise in a certain percentage of patients, many of them directly related to the electrical generator or the transvenous lead wire system and include problems associated with infection, pocket hematoma, pneumothorax, lead fracture, dislodgement and vascular access limitations.

2. Conventional right ventricular apical pacing alters the normal synchronization of different heart chambers, and may adversely influence ventricular function, leading to heart failure and increased mortality.

3. Single chamber ventricular systems are generally limited to patients with atrial fibrillation and slow ventricular response where the patient does not require frequent pacing. Frequent ventricular apical pacing has been shown to be deleterious to cardiac function. There are numerous conditions that would preclude the implantation of a transvenous pacemaker system, such as compromised venous access, the need to preserve veins for hemodialysis, thrombosis, a patient's history of infection, or the need for an indwelling venous catheter.

4. Conventional pacemaker generators permit sensing of electrical cardiac action by use of electrodes embedded in the endocardium or vascular structures of the heart. Without the electrodes, generators are unable to detect electrical cardiac action. For a wireless system, it would be desirable for generators to detect and induce electrical action. Such prior art conventional generators are generally disk-shaped and may not be suitable for operability within the vascular system. An electrical generator embedded within an electrically conductive shaft coupled in itself to the electrodes would be desirable to conform to the intravascular contour and provide proximity to cardiac conduction tissue structures for transfer of electrical/ultrasound/Doppler/infrared and magnetic signals.

5. Biventricular pacing or resynchronization requires the placement of electrodes within the venous system of the heart. However, other than lodging the tip of the lead into the distal coronary vein, there has been found no safe anchoring mechanism to maintain the lead from dislodging. Additionally, the optimum lodging site may not be the ideal pacing location for effective myocardial stimulation. Screw-in anchors may be applied to the myocardium, but cannot be utilized in vascular structures due to the risk of endothelial damage and hemorrhage.

6. Conventional pacemaker right ventricular leads have to cross the tricuspid valve to reach the right ventricular endocardium. Such leads may cause unwanted tricuspid regurgitation by interfering with tricuspid valve closing during heart contraction leading to ineffective ventricular contraction that may interfere with the right ventricular function. Pacing of the His bundle, the heart muscle cells specialized for electrical conduction, has been shown to provide more physiologic pacing, however, the pacemaker leads have to traverse the tricuspid valve.

These and other disadvantages are addressed by one or more embodiments of the present invention. In accordance with the present invention, an implantable device and system is provided which serves to sense, pace, and shock various cardiac tissues. The subject system employs electrodes that are suitable for vascular structures such as a venous or arterial system using leads of different configurations. The leads are collapsible in a pre-deployment configuration and self-expand for deployment once positioned at the desired location.

Preferably, a pacemaker lead system generally comprises a series of curvilinear electrodes which self-expand when extruded from the steerable delivery catheter, and may be folded back into the delivery catheter by pulling on the shaft and electrodes. Each pair of curvilinear electrodes may overlap with each other before deployment, and fan out when deployed, in order to conform to the shape of the vascular or cardiac structure at which it is deployed. This facilitates endothelialization of the electrodes by the body fluids and cells. The pacemaker has a proximal and a distal end. There is an opening at the proximal end that may be used to extract the pacemaker system. There is a constriction just distal to the proximal end that may be used as a backup system for extraction, using a snare used to extract pacemakers. The distal parts of the shaft of the pacemaker as well as the electrodes are equipped with piezoelectric crystals to enable pacing with ultrasound energy.

The energy source or electrical generator for the electrodes may be contained within a relatively flexible and electrically conductive shaft of the system that is connected to the electrodes and obviates the need for external source of energy or electricity.

Thus, the subject system senses and generates electrical energy to and from tissue within a mammalian body. The system includes an electrically conductive shaft that is inserted within the mammalian body and has a defined shaft axis line. An electrical generator is embedded within the flexible and electrically conductive shaft for producing and sensing electrical and nonelectric signals. An electrically conductive expandable electrode is connected to the electrically conductive shaft. The expandable electrode is radially displaceable with respect to the shaft axis line that defines a longitudinal direction for contiguous contact with a wall of the tissue. The expandable electrode includes a pair of arcuate arm members that extend at an angle of less than 90 degrees with respect to the longitudinal direction from opposing sides of the electrically conductive shaft. The angle facilitates withdrawal of the unfolded electrodes back into the catheter delivery system for change in location or withdrawal. Two or more arcuate arm members have overlapping sections prior to the radial expansion of the electrically conductive self-expandable electrode with the two or more arcuate arm members located in a substantially oblique plane, each with respect to the other. The two arm members are self-displaceable once outside the steerable catheter delivery system. Nonelectric sensors may be incorporated within the pacemaker generator or shaft, or may be located at a distance within the body of the patient and transmit signals to the microprocessor wirelessly.

The subject system is in the area of sensing myocardial electrical impulses as well as non-electrical cardiac and vascular input such as mechanical heart motion, intra-cardiac and intravascular blood flow, intra-cardiac and intravascular pressure, as well as non-cardiovascular data such as body motion or activity (resting or exercising) and body position (recumbent, standing or ambulating) during abnormal cardiac rhythm. Based on an algorithm that uses one or more of these parameters, the microprocessor selects appropriate response of pacing, shocking or continuing to monitor before further action. Therapy thus provided uses low/high voltage pacing and defibrillation.

The subject system may provide for defibrillation only in certain body positions such as recumbent or semi-recumbent, and solely during lack of vigorous activities or strenuous exercise, in order to avoid inappropriate shock. Thus in the event of suspected life-threatening arrhythmias received by the microprocessor, the system will not shock the patient while in the upright position as with jogging or sports, or even in the recumbent position if associated with vigorous activities such as during sexual intercourse. The system will deliver the shock once exercise ceases and recumbent or semi-recumbent position is achieved.

The subject system also provides for pacing of the His bundle and ventricles by way of the tributaries of the coronary sinus and cardiac veins that drain the His bundle and left ventricle. This physiologic method of cardiac pacing may be wireless, or by way of conventional extra-cardiac generator and pacemaker lead system, without the need to traverse the tricuspid valve.

The subject system also provides for pacing of the His bundle and ventricles without the need for an embedded generator by passively transmitting electrical impulses from the atria via electric conducting shaft and electrodes that extend from the atria proximally to the distal electrode in the cardiac venous system. In the presence of complete AV block, impulses generated by the atria are able to pass through an implantable pacemaker system that replaces a non-functioning bundle of His. The conducting elements in the pacemaker system are controlled by a microprocessor that allows normal atrial impulses to pass through to the His bundle and ventricles and slows down fast impulses originating in the atria as during atrial tachycardia or atrial fibrillation by way of resistors. Pacing impulses are unidirectional by way of diodes or other unidirectional electronic devices such as transistors or the like in order to prevent retrograde ventricular atrial conduction. Piezoelectric crystals permit backup pacing in the absence of heart rhythm. Thus the pacemaker system may act as an implantable His bundle operating from the venous system of the heart.

The subject system is further directed to the field of permitting pacing using electric, ultrasound, or magnetic stimulation permitting wireless stimulation of the tissue. The subject system concept is further directed to the field of providing simultaneous pacing of right atrial, left atrial, left ventricle and the bundle of His by way of intravascular electrodes for providing physiological pacing, treating heart failure and provides for a homogeneous electric field for defibrillation.

Figure 2:
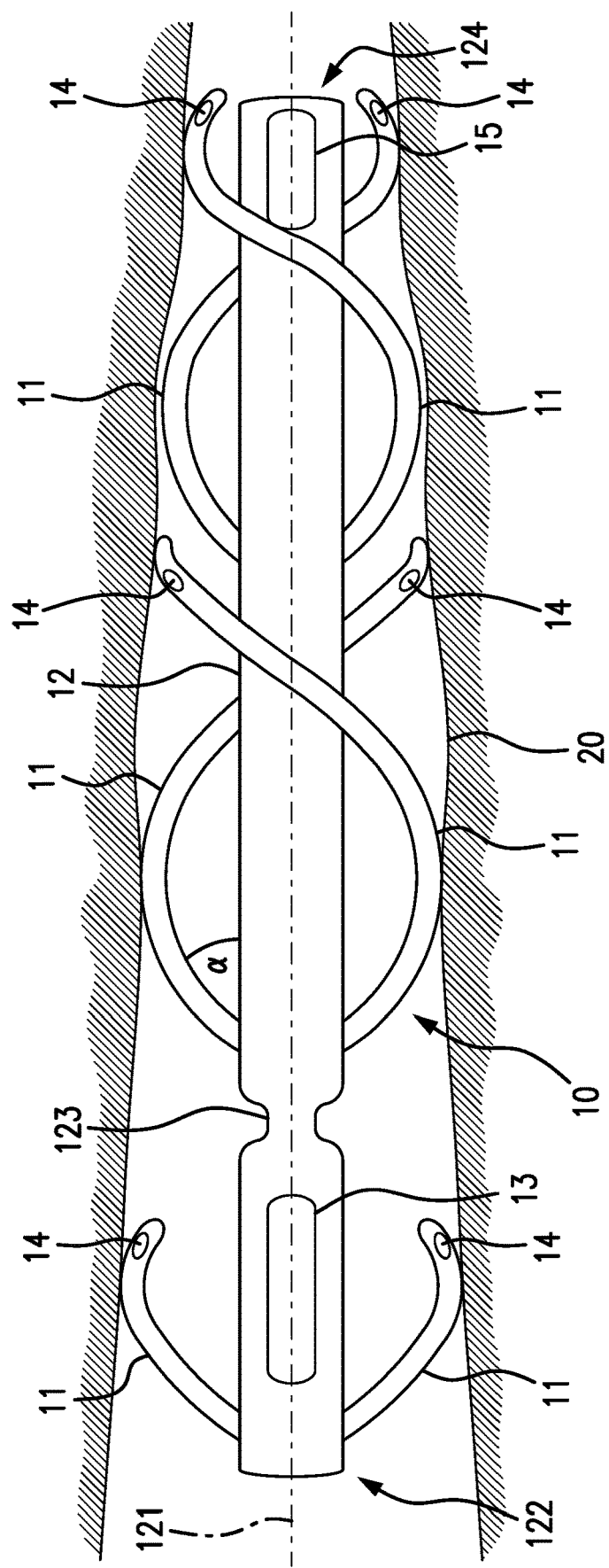
FIG. 2 is a schematic perspective view illustrating a system for generating and sensing electrical energy to and from tissue within a mammalian body, in a deployed configuration, according to an embodiment of the invention.
Figure 3:
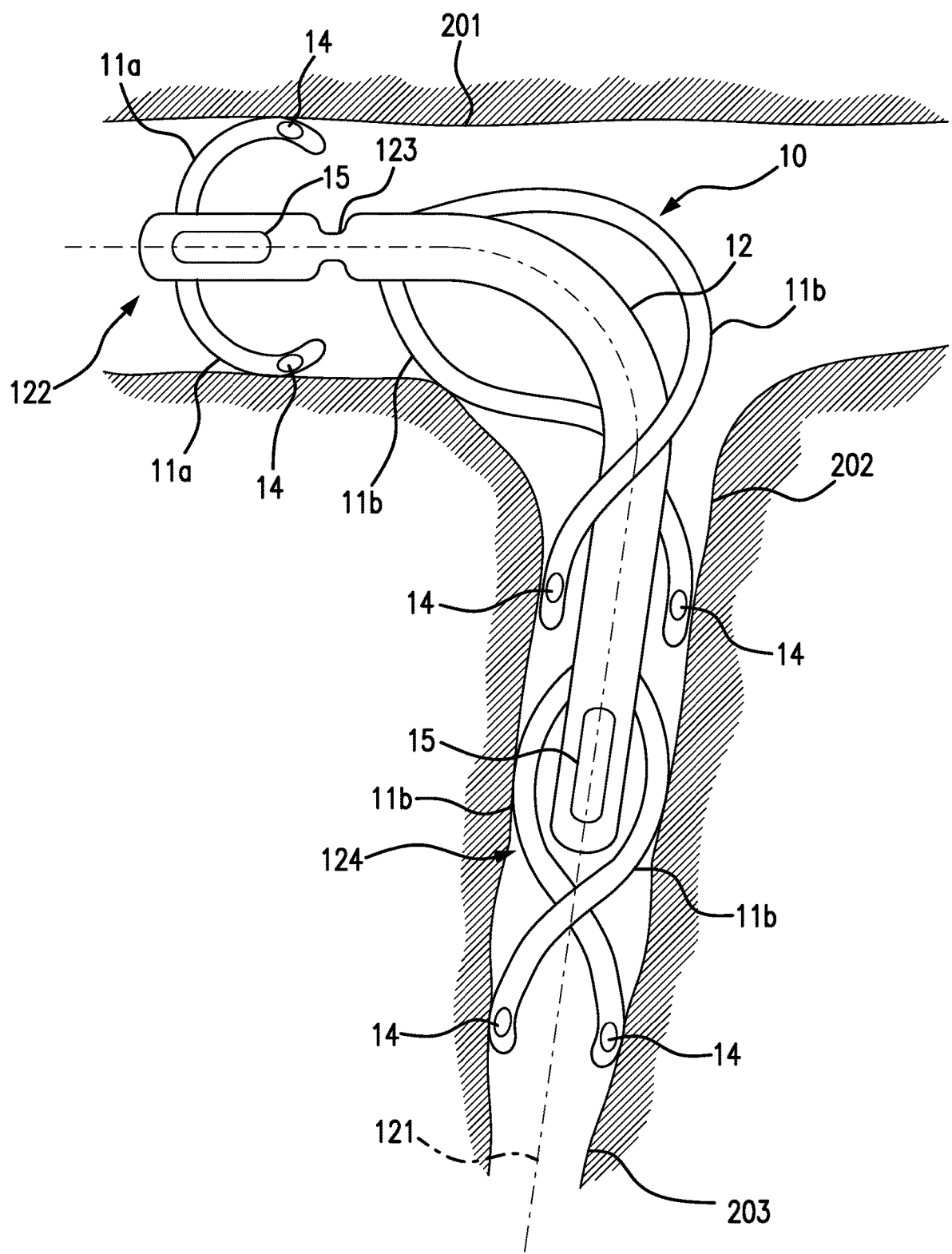
FIG. 3 is a schematic perspective view illustrating a system for generating and sensing electrical energy to and from tissue within a mammalian body, in a deployed configuration within a small tributary of the coronary sinus draining the bundle of His, according to an embodiment of the invention.

Referring now to FIGS. 1-3, there is shown a system for generating, applying, and sensing electrical energy to and from tissue within a patient's body, such as the wall of a vessel 20 within the patient's body. It is noted that the invention is not limited to human patients; in various applications, "patients" may include but are not limited to mammals of all kinds, as well as other creatures, living or dead, with tissue which will be stimulated to react to the application of electrical or other energy.

Preferably, the system includes a pacemaker lead system 10, which includes an electrically conductive lead or shaft 12 insertable within the vessel 20 or in proximity to mammalian tissue within a patient's body. (For brevity, the electrically conductive lead or shaft 12 will be termed a "shaft" going forward.) The shaft 12 defines an axis line 121, which in some embodiments is curvilinear as shaft 12 may be inserted into the patient's body in a tortuous contour. The shaft 12 preferably has a low or flat profile so as to minimally interfere with blood flow yet maintain close contact with the lining of the surrounding tissues (such as blood vessels or heart chambers). In some embodiments, the shaft 12 has a curved profile, as depicted in FIG. 3, to conform to the inner vascular contour of a vessel 20. For the same reasons, the shaft is preferably flexible to accommodate vessel contours.

The system includes at least one generator adapted to be received within the body of the patient, preferably in the coronary sinus 201 and tributary veins 202 supplying the His bundle and cardiac muscle. In a preferable embodiment, the system includes a generator 13 embedded near the proximal end 122 of the shaft 12, as shown in FIG. 1. In certain embodiments, the generator 13 is powered by a battery, while in alternate embodiments the generator 13 is powered by a stimulator that produces electrical current via body tissue without the need for a wire lead.

In certain embodiments, the embedded generator 13 produces electrical stimulation to the shaft 12, and to electrodes 11 in contact with the shaft 12. In alternate embodiments, the generator 13 produces ultrasound energy that is transmitted to the electrodes equipped with receiver transducer circuitry operable to convert ultrasound energy to electric energy, for transmission to the electrodes 11. In either case, an important advantage of embedding generator 13 within shaft 12 is that the embedded generator 13 minimizes interference with the ultrasonic or electrical signals.

Additionally, a secondary electrical generator (not depicted) is preferably located external to the patient's body, for wireless transmission of electrical energy to piezoelectric elements 14a within the electrodes 11, as will be discussed in following paragraphs. This secondary generator serves as a backup energy source in the event that the embedded generator 13 fails. In alternate embodiments, one or the other of the generators is omitted, or additional generators are placed inside or outside the body.

The pacemaker lead system 10 preferably includes elements for ultrasonic pacing ultrasonic and Doppler imaging, low voltage pacing, and high voltage pacing. In certain embodiments, the embedded generator 13 itself is operable to detect cardiac electrical activity, without the use of intra-cardiac electrodes. For example, in certain embodiments, the embedded generator 13 is operable to emulate a 12-lead electrocardiogram by detecting cardiac electrical activity from various locations of the heart; to detect cardiac mechanical activity by way of ultrasound or Doppler signals; to detect body position, body activity and respiration using prior art sensors in order to provide appropriate cardiac shock at certain body positions, lack of activities or lack of respiration; and/or to receive signals from pressure sensors within the heart and vascular system in order to determine the need to provide appropriate cardiac shock in the event of absence of pressure indicating a life-threatening cardiac arrhythmias.

The embedded generator 13 can then, based on the received cardiac, electrical, and mechanical inputs, synchronize output signals to electrodes implanted in various cardiac chambers in order to provide optimal cardiac contraction and function. It is noted that, in certain embodiments, the embedded generator 13 produces either cardiac electrical signals or ultrasound signals inducing cardiac mechanical contraction without use of electrodes.

In alternate embodiments, a microprocessor is operable to detect nonelectrical activity of the heart and body such as cardiac wall motion, cardiac and vascular blood flow, cardiac and vascular pressure, body position and body activities, in a wireless fashion. The microprocessor is in various embodiments inside or outside the embedded generator 13. The microprocessor senses electrical and nonelectric signals passing from the wall of a mammalian vessel 20 or tissue within a patient's body, and produces electric energy that passes through the wall of the vessel 20 to the cardiac conduction tissue.

Preferably, sensors for this detection are incorporated within the pacemaker lead system 10. Extra-cardiac non-electric sensors transmit data wirelessly to the microprocessor. In various embodiments, non-electric sensors include but are not limited to cardiac sensors detecting activity such as chamber wall motion, cardiac muscle contraction, tissue doppler imaging, cardiac chamber blood flow, and cardiac chamber cavity pressure, as well as sensors for tissue doppler imaging; vascular sensors detecting activity such as intravascular and/or extravascular (arterial) blood flow, intravascular and/or extravascular blood pressure, and arterial pulse; and body sensors detecting activity such as body position (e.g. recumbent, semi-recumbent, standing), body activity (e.g. resting, exercising), and respiration rate. Additionally, in certain embodiments, electric sensors detect cardiac depolarization and repolarization. A defibrillation algorithm can take input from any of these sensors as a basis for a determination whether to actuate defibrillation.

Various preferable embodiments of the microprocessor, generator, and sensors are described more completely in U.S. patent application Ser. No. 15/691,924 and its parent applications, which as noted previously are incorporated by reference.

In preferred embodiments, embedded generator 13 has a maximum of 0.63 cm$^3$ volume and measures a maximum of 5.0 cm in length, 0.5 cm in width, and 0.25 cm in height. Embedded generator 13 is thereby easily insertable within the coronary sinus 201 (which measures about 7.0 cm in length, with a 0.7 cm diameter and has a 2.0 cm circumference. Suitable commercially-available miniature generators include but are not limited to Nanostim® and Micra®.

The pacemaker lead system 10 further includes a plurality of self-expandable electrodes 11 coupled to the shaft 12 on opposing sides thereof, each displaced from the other by a predetermined distance as depicted in FIGS. 1 and 2. It is noted that, while the figures depict six electrodes 11, this number is not limiting.

Preferably, the electrodes 11 include ultrasound and electromagnetic receiver electrodes. Each of the electrodes 11 are electrically coupled to shaft 12, which is electrically conductive. The electrodes 11 are preferably bipolar with a distal cathode and a proximal anode, and formed of suitable compositions such as iridium, platinum, or like composition which provide optimal sensing, pacing or shock. As with the shaft 12, the electrodes 11 are preferably flexible so as to adjust to the shape of the surrounding vessel 20 and other tissues. In a preferable embodiment, the electrodes 11 are fabricated by an elastic metal such as iridium or platinum to allow expansion when a deployment catheter 31 (described further herein) is withdrawn. Additionally, the electrodes 11 are preferably either made of or coated with one or more materials having drug eluting properties, and which are resistant to thrombus formation; suitable materials with these features are well-known in the art.

Electrodes 11 are radially displaceable from the distal end of the shaft 12, forming an angle $\alpha$ of less than 90 degrees with respect to axis line 121, and thereby providing contiguous contact with the patient's tissue or an inner wall of the vessel 20 when the pacemaker system 10 is in the deployed mode of operation. Over time, this style of contact allows vascular endothelium to cover the electrodes 11 so that they become part of the vessel wall, securing them in place. The acute angle $\alpha$ also facilitates withdrawal of the pacemaker back into a steerable deployment catheter 31 (described below) to adjust placement for optimum sensing and pacing, or to extract entirely. It is noted that angle $\alpha$ varies depending on the exact position of the pacemaker system 10 relative to the vessel walls, but is always acute to provide the contiguous contact. Preferably, the electrodes 11 are curvilinear and therefore more easily deployed to such an angle.

In various embodiments, the electrodes 11 have an oval cross-sectional shape, a rectangular cross-sectional shape, or other suitable shapes known in the art.

Compared to prior art, the described arrangement of electrodes provides such advantages as closer electrode contact with a larger surface area of tissue. With a greater surface area of electrodes, less energy is needed to stimulate tissue. Additionally, flat shaped electrodes are provided in a preferred embodiment (compared to the round cylindrical shaped conventional electrodes) for more effective endothelium coverage, minimizing the risk of clot formation or infection.

FIG. 1 depicts the pacemaker lead system 10 in the pre-deployment stage, with electrodes 11 in overlapping relation to minimize the cross-sectional area for insertion into the vessel 20. FIG. 2 depicts the pacemaker lead system 10 in a deployed position subsequent to expandable electrodes 11 being radially expanded. As FIG. 2 illustrates, in its deployed position, the radially expanded electrodes 11 contiguously contact an inner wall of vessel 20 and collectively act as an anchoring mechanism.

Preferably, the electrodes 11 are organized into groupings of two or more electrodes which are evenly distributed around a circumference of the shaft 12. For example, as depicted in FIGS. 1 and 2, the pacemaker lead system 10 has three groups of two electrodes each, and the two electrodes in each group are disposed at opposing sides of the shaft 12. As a result, each pair of electrodes comes in contact with both sides of the vessel 20 when expanded, more firmly anchoring the pacemaker lead system 10 and optimizing distribution of the signals through the vessel 20. Those of ordinary skill in the art will see that the same principles may be applied to groupings of three or more electrodes.

The electrodes 11 are preferably formed of a suitable metal composition for transmission of electrical energy. Said metal composition is suitable if it is electrically conductive, expandable in the oblique radial direction, possesses sufficient structural integrity to support the forces applied thereto during expansion and during operation within the patient's body, and is biocompatible with respect to the patient's body. Many such compositions are well known in the art and will not be further discussed in detail, but include iridium and platinum.

In a preferred embodiment, the electrodes 11 have embedded within, or otherwise affixed thereto, piezoelectric elements 14a such as piezoelectric crystals. Because the piezoelectric effect is reversible, piezoelectric materials or compositions exhibit internal generation of electric charge resulting from an applied mechanical force, as well as internal generation of mechanical strain resulting from an electric field such as from electrical generator 13 embedded in electrically conductive shaft 12. Piezoelectric elements 14 may be formed of well-known compositions including but not limited to barium titanate and lead zirconate titanate, which exhibit larger displacements while inducing larger electric voltages than found in natural monocrystalline materials.

In some embodiments, one or more additional piezoelectric elements, such as piezoelectric element 14b, are embedded in the shaft 12 itself. In the embodiment depicted in FIG. 3, piezoelectric elements 14a and 14b are sufficient to operate the system in lieu of the embedded electrical generator 13, which is therefore not included.

In certain embodiments, the electrodes are also equipped with receiver transducer circuitry of any suitable type known in the art capable of converting ultrasound energy to electric energy to be transmitted to the electrodes.

In this manner, the pacemaker lead system 10 both generates and senses electrical energy to and from mammalian tissue within a patient's body and/or the walls of the patient's vessel 20. Electrical generator 13, and/or piezoelectric elements 14a and 14b, thus produce and sense electrical energy passing to and from the vessel 20.

In accordance with a preferred embodiment of the present invention, wireless piezoelectric elements 14a, 14b are thereby implanted within the vascular or muscular structures of the vascular system. Their stimulation by external or implantable ultrasound and Doppler transmitter measures allow for transduced wireless stimulation of the tissues, when the piezoelectric elements convert their externally stimulated mechanical energy to electrical energy. A self-retaining wireless implantable electrode system operable in this manner with piezoelectric elements is heretofore unseen.

Conventional pacemaker generators permit sensing of electrical cardiac action by use of electrodes imbedded into the endocardium or vascular structures of the heart. Without electrodes, generators are unable to detect electrical or mechanical cardiac action. For a wireless system, it would be desirable that generators serve both to detect and induce electrical action. In addition, conventional generators are disc shaped and may not be suitable for use within the vascular system. A pacemaker system having a low profile flexible structure with curved and elongated electrodes would be more desirable to conform to the intravascular lumen space and permit close proximity to cardiac structures for effective transfer of electrical, ultrasound, Doppler, infrared and magnetic signals.

Preferably, as depicted in FIG. 1, a steerable deployment catheter 31 houses the pacemaker lead system 10, with electrodes 11 folded into a compressed position prior to placement of the pacemaker lead system 10. The pacemaker lead system 10 is tethered at its proximal end 122 to a delivery catheter 32. The delivery catheter 32 has an adapter 321 that extends from the neck 322 of the delivery catheter 32, which fits into a proximal aperture 125 of the pacemaker lead system 10 and locks into a shelf 126 to create a firm seal that is in locked position during the insertion of the lead system 10. The lock is released once the lead system 10 is in an optimum position within the vessel 20. The release is accomplished from the proximal portion of the delivery catheter 32 (not depicted), which remains outside the patient's body and is withdrawn together with the deployment catheter 31 upon conclusion of the delivery.

The steerable deployment catheter 31 is introduced into the vascular system using standard techniques over a flexible wire system, or may be equipped with flexible wire of its own (not depicted), so as to deliver and position the pacemaker lead system 10. The same catheters are also suitable for retrieval of the pacemaker lead system 10. The shelf 126 within the aperture 125, as well as a construction point 123 near the proximal end 122 of the lead system 10, allow for withdrawal of the lead system 10, using prior art retrieval systems such as snares to grasp the lead system 10 at one or both locations.

FIG. 2 illustrates the electrodes 11 in their deployed configuration. They may be placed in such configuration once the steerable deployment catheter 1 is completely withdrawn, whereby the oblique ring electrodes 11 are expanded to closely conform to the shape of the vessel 20 or chamber that needs to be stimulated. Contact with the lining of the vessel or chamber is essential for body fluids to flow freely and tissue to grow to cover the electrodes 11 with endothelium (lining of the vessels), such that clot formation may be prevented. Preferably, the electrodes 11 are self-expanding when the steerable deployment catheter 31 is completely withdrawn, due to an internal elasticity of the electrode material and/or positioning, and the compression previously applied by the steerable deployment catheter 31. Additionally, by returning the steerable deployment catheter 31 to surround the shaft 12, the electrodes 11 are pressured back into their pre-deployment position, releasing the walls of the vessel 20 and allowing for easy removal.

FIG. 3 illustrates the pacemaker lead system 10 deployed in a coronary sinus 201 and tributary vein 202 after complete withdrawal of the steering catheter delivery and deployment catheters 32, 31, with electrodes 11 extending beyond a distal end 124 of the shaft 12 in order to reach small coronary veins 203 draining the bundle of His. Close proximity to the His bundle allows pacing of the ventricles from an optimal location, without the need for traversing the tricuspid valve or right ventricular cavity, thereby minimizing complications known to occur with right ventricular pacemakers such as perforation, irritation, arrhythmias, clot formation, tricuspid regurgitation, pulmonary embolism, as well as traditional intravascular lead and subcutaneous generator complications.

When deployed as depicted in FIG. 3, the pacemaker lead system 10 acts as a passive controlled conduit of electricity from the atria to the ventricles controlling the rate, speed, and direction of impulses delivered to the His bundle and ventricles. Diodes are used when unidirectional conduction is desired.

In certain embodiments, electric conduction through the pacemaker lead system 10 is deliberately slowed down. In the depicted embodiments, this delay is introduced by reducing the diameter of the shaft 12 at a constriction point 123; other constriction points are also added to the shaft 12 or electrodes 11 in certain embodiments. Additionally, or in the alternative, certain embodiments add resistors or timers within the conduction system. This delay allows activation of the atria by proximal electrodes 11a coupled nearest to the embedded generator 13, before the impulse is delivered to the His bundle and ventricles by distal electrodes 11b coupled closer to the distal end 124 of the shaft, and permits efficient contraction of the entire cardiac muscle to optimize blood flow through its chambers. By activating the atria before the ventricles, the ventricle is filled before ventricular contraction begins. Delaying conduction using timers or resistors also slows conduction along the shaft 12 by abnormally fast heart rhythm, as in tachycardia, atrial fibrillation, or flutter.

Using the disclosed system, a convenient and effective method of securely implanting a pacemaker lead into the vascular system (veins, arteries or lymphatic channels) of the heart is available.

Preferably, a steerable catheter is introduced into the venous system of the heart, implanting electrodes at various locations within the cardiac veins for optimal pacing. The locations are determined by the resultant pacing induced electrical and mechanical efficiency. Conventional steering mechanisms are utilized for introducing pacemaker leads and maneuvering in different cardiac chambers and vessels. Steerable flexible wire systems may be introduced via the deployment catheter. The electrodes are preferably detachable and embedded in the lining of the vessel.

In certain other embodiments, the electrodes are located in vascular beds of each of the four cardiac chambers in order to provide homogeneous electrical stimulation and defibrillation.

In comparison to the present invention, various embodiments of which have been disclosed above, prior art devices generally do not provide for contiguous atrial and ventricular intravascular pacing or His bundle pacing, do not present a low profile design, and do not have a variable electrode orientation capability. See Table 1. Prior pacemaker systems also rely solely on electric sensors before delivering pacing or shock treatment. No prior art pacemaker or defibrillator relies on a combination of electric and non-electric sensors before providing therapy.

TABLE 1

Features of Leadless Pacemaker Devices (LPD)

| Features | LPD* | Present Invention |
| --- | --- | --- |
| Battery within device | Yes | Yes |
| Steerable catheter delivery | Yes | Yes |
| Reattachable extraction mechanism | Yes | Yes |
| Electric algorithm | Yes | Yes |
| Nonelectric algorithm | No | Yes |
| Self expanding electrodes | No | Yes |
| Helical fixation/Tines | Yes | No |
| Contiguous A and V pacing# | No | Yes |
| Ideal for Bi-V pacing | No | Yes |
| Suitable for His bundle pacing | No | Yes |
| Coronary sinus/vein use | No | Yes |
| Low profile design | No | Yes |
| Overlapping electrodes | No | Yes |
| Variable electrode orientation | No | Yes |
| Flexible design | No | Yes |

*Leadless Pacing Device: U.S. Pat. Nos. 5,814,089; 6,522,915 B1; 6,584,352 B2; 8,923,963 B2; 9,072,914 B2.
A = atrial, V = Ventricular The descriptions above are intended to illustrate possible implementations of the disclosed system, and are not restrictive. While this disclosure has been made in connection with specific forms and embodiments thereof, it will be appreciated that various modifications other than those discussed above may be resorted to without departing from the spirit or scope of the disclosed system. Such variations, modifications, and alternatives will become apparent to the skilled artisan upon a review of the disclosure. For example, functionally equivalent elements or are substitutable for those specifically shown and described, and certain features are usable independently of other features. Additionally, in various embodiments, all or some of the above embodiments are selectively combined with each other, and particular locations of elements are reversed or interposed, all without departing from the spirit or scope of the disclosed system as defined in the appended claims. The scope should therefore be determined with reference to the description above and the appended claims, along with their full range of equivalents.

What is claimed is:

1. A system for applying and sensing electrical energy to and from tissue within a patient's body, the system comprising:
   a flexible shaft having a proximal end and a distal end, and insertable within the patient's body, said shaft defining a shaft axis line;
   a plurality of self-expanding electrodes electrically coupled to an electrical source, each self-expanding electrode of said plurality thereof having a first end coupled to said shaft and a second end extending towards said distal end of said flexible shaft and separated from said first end a length of said each self-expanding electrode,
   wherein an angular displacement of said each self-expanding electrode at said first end thereof from said shaft is less than 90°,
   wherein said each self-expanding electrode extends helically along and around said flexible shaft in an antegrade dispositional relation therewith, and
   wherein said each self-expanding electrode is radially expandable with respect to the shaft axis line from a compressed position to an expanded position into a contiguous contact with a wall of a tissue of the patient's body substantially along said length of said each self-expanding electrode, said each self-expanding electrode being configured to conduct electrical signals from said electrical source into the wall of the tissue of the patient's body when in contact with the wall; and
   a steerable delivery catheter for insertion into a vascular system of the patient, said delivery catheter surrounding said electrodes and said flexible shaft and applying a pressure to said electrodes to thereby restrain said electrodes in the compressed position while within said delivery catheter, wherein said electrodes and said flexible shaft are removable from said delivery catheter,
   wherein said electrodes are elastically self-expanded to the expanded position when removed from said delivery catheter.

2. The system as recited in claim 1, wherein said shaft is formed of an electrically conductive composition for electrical communication with said electrodes.

3. The system as recited in claim 1, wherein said electrodes are disposed in substantially curvilinear planes each with respect to the other, and said electrodes overlap with respect to the other while in the compressed position.

4. The system as recited in claim 1, wherein said electrodes are disposed on at least opposing sides of said shaft.

5. The system as recited in claim 1, wherein said electrical source is an electrical generator embedded within said shaft.

6. The system as recited in claim 1, wherein said electrical source is an element with a piezoelectric composition embedded within said shaft.

7. The system as recited in claim 1, wherein the flexible shaft includes a constriction point, at least one distal electrode disposed between said distal end of said shaft and said constriction point, and at least one proximal electrode disposed between said proximal end of said shaft and said constriction point.

8. The system as recited in claim 7, wherein
   said flexible shaft is configured to be inserted within a vessel of the patient's body so as to contact a coronary sinus with the at least one proximal electrode and to contact coronary veins with the at least one distal electrode, and
   wherein, when said electrical source is a patient's atria, the system thereby acting as a controlled passive conduit of normal electric impulses generated by the atria for transmission to a His bundle.

9. The system as recited in claim 1, wherein each of said electrodes is selected from the group consisting of high voltage pacing electrodes, low voltage pacing electrodes, and parameter sensing electrodes.

10. The system as recited in claim 1, wherein said each electrode has embedded therein elements having a piezoelectric composition.

11. The system as recited in claim 1, wherein said each electrode is at least partially formed of a piezoelectric composition.

12. The system as recited in claim 1, wherein said electrical source includes an ultrasound and Doppler source for pacing in proximity to said electrically conductive electrode.

13. A system for applying and sensing electrical energy to and from tissue within a patient's body, the system comprising:
   a flexible shaft having a proximal end and a distal end insertable within the patient's body, said flexible shaft defining a shaft axis line;
   an electrical source embedded within said shaft; and,
   a plurality of self-expanding electrodes electrically coupled to said electrical source, each self-expanding electrode of said plurality thereof having a first end coupled to said shaft and a second end extending towards said distal end of said flexible shaft and separated from said first end a length of said each self-expanding electrode, wherein an angular displacement of said each self-expanding electrode at said first end thereof from said shaft is less than 90°, wherein said each self-expanding electrode extends helically along and around said flexible shaft in an ante grade dispositional relation therewith, and wherein said each self-expanding electrode is radially expandable with respect to the shaft axis line from a compressed position to an expanded position into a contact with a wall of a tissue of the patient's body substantially along said length of said each self-expanding electrode in multiple radial planes, said each self-expanding electrode being configured to conduct electrical signals from said electrical source into the wall of the tissue of the patient's body when in contact with the wall.

14. The system as recited in claim 13, wherein said shaft is formed of an electrically conductive composition for electrical communication with said electrodes.

15. The system as recited in claim 13, wherein said electrodes are disposed in substantially curvilinear planes each with respect to the other, and said electrodes overlap with respect to the other while in the compressed position.

16. The system as recited in claim 13, wherein said electrodes are disposed on at least opposing sides of said shaft.

17. The system as recited in claim 13, wherein said electrical source is an electrical generator embedded within said shaft.

18. The system as recited in claim 13, wherein said electrical source is an element with a piezoelectric composition embedded within said shaft.

19. The system as recited in claim 13 further comprising:
a microprocessor operatively coupled to said self-expanding electrodes, and non-electrical sensors operatively coupled to said microprocessor and configured to detect at least the patient's body position and body activity, wherein said electrodes are operated by said microprocessor executing a defibrillation algorithm, the defibrillation algorithm receiving input from said non-electrical sensors and selecting a therapy routine based on at least the detected body activity and the detected body position.

20. A system for generating and applying ultrasound energy to tissue within a patient's body, the system comprising:

a flexible shaft having a proximal end and a distal end, and insertable within the patient's body, said shaft defining a shaft axis line;

an ultrasound energy source embedded within said shaft; and, a plurality of self-expanding electrodes electrically coupled to said ultrasound energy source, each self-expanding electrode of said plurality thereof having a first end coupled to said shaft and a second end extending towards said distal end of said flexible shaft and separated from said first end a length of said each self-expanding electrode, wherein an angular displacement of said each self-expanding electrode at said first end thereof is less than 90°, wherein said each self-expanding electrode extends helically along and around said flexible shaft in an ante grade dispositional relation therewith, and wherein said each self-expanding electrode is radially expandable with respect to the shaft axis line from a compressed position into a contiguous contact with a wall of a tissue of the patient's body substantially along said length of said each self-expanding electrode in multiple radial planes, said each self-expanding electrode being configured to conduct ultrasound energy signals from said ultrasound energy source into the wall of the tissue of the patient's body when in contact with the wall.

* * * * *